United States Patent [19]

Heimke et al.

[11] 4,004,581

[45] Jan. 25, 1977

[54] TOOL FOR FORMING A BED IN A HIP BONE TO RECEIVE AN ARTIFICIAL ACETABULUM

[75] Inventors: Günther Heimke, Mannheim; Peter Griss, Plankstadt; Hanns Von Andrian Werburg, Ilvesheim; Paul Wachter, Mannheim, all of Germany

[73] Assignee: Friedrichsfeld GmbH, Mannheim, Germany

[22] Filed: Sept. 9, 1975

[21] Appl. No.: 611,782

[30] Foreign Application Priority Data

Sept. 11, 1974 Germany .......................... 2443450

[52] U.S. Cl. .............................. 128/92 E; 128/305; 3/1.912
[51] Int. Cl.² ................... A61B 17/16; A61B 17/32
[58] Field of Search ........ 128/92 E, 92 EA, 92 EB, 128/92 EC, 92 R, 83, 305, 92 C, 92 CA; 3/1.9–1.913

[56] References Cited

UNITED STATES PATENTS

| 3,633,583 | 1/1972 | Fishbein | 128/305 |
| 3,667,456 | 6/1972 | Charnley | 128/92 R |
| 3,702,611 | 11/1972 | Fishbein | 128/305 |
| 3,894,297 | 7/1975 | Mittelmeier | 3/1 |

OTHER PUBLICATIONS

"Complete Replacement Arthroplasty of the Hip by the Ring Prosthesis" by P. A. Ring, *The Journal of Bone & Joint Surgery*, British vol. 50B, No. 4, Nov. 1968, pp. 720–731.
Prosthetic Heads, Tools & Instruments by Zimmer (Advertisment p. 5), Zimmer Mfg. Co., Warsaw, Ind., *The Journal of Bone & Joint Surgery*, vol. 34–A, Apr. 1952, No. 2.

*Primary Examiner*—Ronald L. Frinks
*Attorney, Agent, or Firm*—George H. Mitchell, Jr.

[57] ABSTRACT

A rotary cutter for making the socket bed for a complete endoprosthesis is slidable on a guide rod, which rod is first inserted into a guide bore which has previously been made in the hip bone. The relative axial position of the cutter with respect to the rod indicates the depth of penetration of the cutter.

10 Claims, 6 Drawing Figures

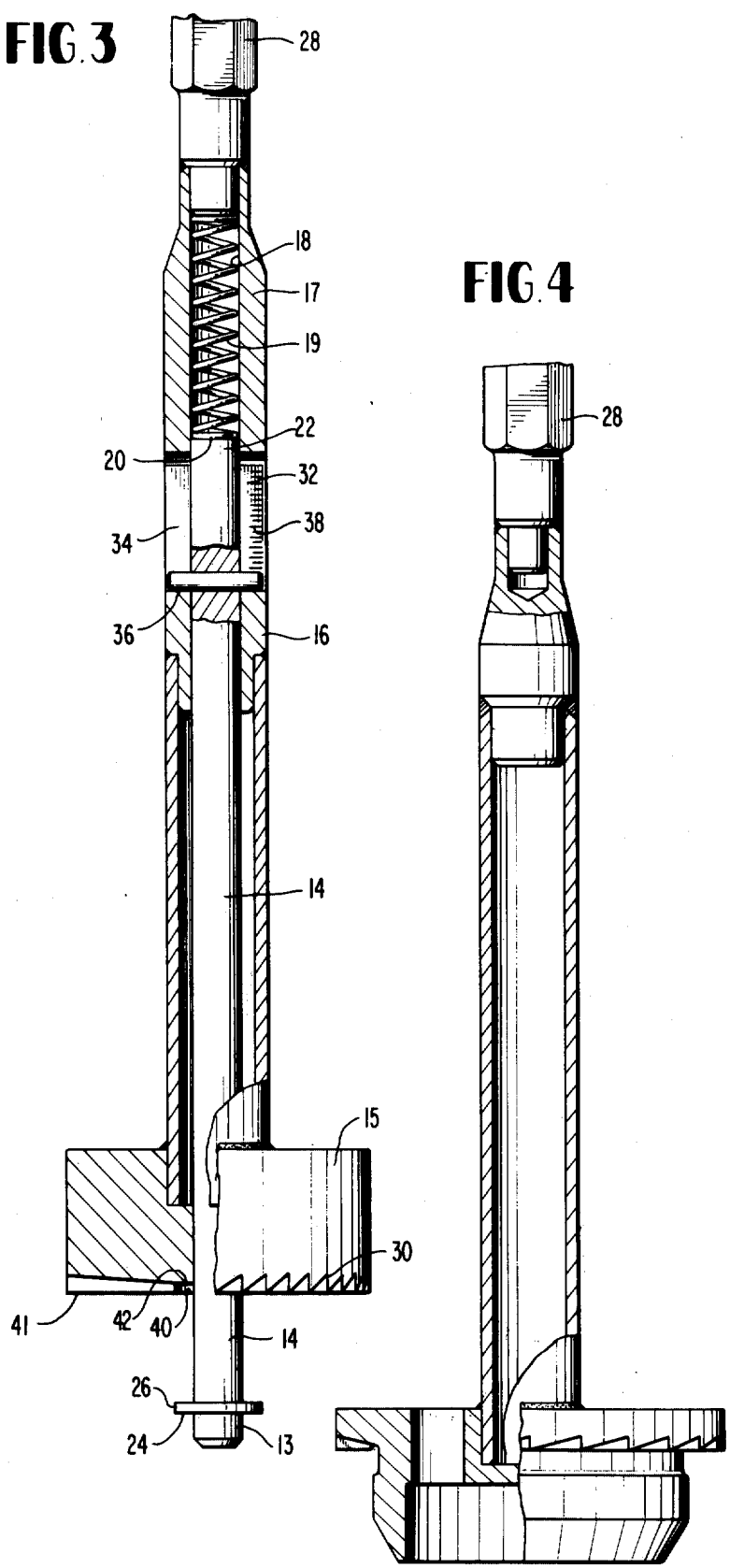

TOOL FOR FORMING A BED IN A HIP BONE TO RECEIVE AN ARTIFICIAL ACETABULUM

The present invention relates to a tool for use in the preparation of a socket bed for the socket portion of a complete hip joint endoprosthesis. The socket may have a threaded exterior surface and the tool may be an end milling cutter or a thread cutter, and it is to be used after an elongated guide bore, having the proper inclination and depth for the socket, has previously been prepared.

In the copending United States Patent Application, Ser. No. 466,640, filed May 3, 1974, now U.S. Pat. No. 3,924,275, a ceramic socket having a screw threaded exterior surface is described and claimed and which is of the type which can be implanted, without the use of cement, in a cylindrical screw threaded socket. The cement-free implantation technique requires that the socket bed be precisely prepared to conform to the shape of the exterior of the socket itself, in order that there will be an initial stability of the positioning of the socket in the bone, this stability being a prerequisite for the growing around and interengagement of the bone tissue surrounding the ceramic socket. For this purpose, after the guide bore has been prepared to the proper depth and inclination of the axis of the socket to be implanted, it is first necessary to enlarge the diameter of the guide bore by means of an end milling cutter to a larger cylindrical or conical diameter and thereafter to cut a thread into the cylindrical or conical wall of the bone cavity thus formed by means of a thread cutter. During the milling of the socket bed, it is possible that the socket may be milled too deeply with the result that a large surfaced perforation of the socket bed can occur. Also, as a result of the necessary pressure exerted during the milling of the cavity, it may also cause the bottom of the socket to break through which, in this case, also, will result in a large surfaced perforation of the bottom of the socket. During the cutting of the thread a relatively large torque must be exerted, and for this reason, it is possible for the surgeon to be unable to notice when the thread cutter has reached the bottom of the socket bed which has previously been prepared by the milling cutter. At this point, if the rotation of the thread cutter is continued and the socket bottom is weak, the cutter can be forced through, with consequences similar to those mentioned above. On the other hand, if the bottom wall of the socket is sufficiently strong to resist penetration, continued rotation of the thread cutter at this point will destroy the thread already cut in the cylindrical wall of the bone.

It is, therefore, among the objects of this invention to avoid the previously described possibility of breaking through the socket bottom into the softer area of the hip tissues and also to prevent the accidental destruction of the thread being cut into the cylindrical wall of the bone.

The foregoing problems are avoided in the present invention by the use of an elongated guide rod so that the relative axial position of the tool with respect to the guide rod acts as a depth gauge to give an indication of the depth of penetration of the tool.

In order to use the tool of the present invention, it is first necessary to drill, or otherwise prepare, a relatively small diametered straight guide bore perforating the hip bone at the desired angle of implantation corresponding to the central axis of the socket. This guide bore serves to control the positioning of all tools to be used in preparing the bed of the socket as well as a drainage relief for blood flowing into the bottom of the socket during actual implantation.

In the operation of the invention, the guide rod is inserted into the guide bore so that its end reaches to the bottom of the bore. During rotation of the end milling cutter in which the guide rod is axially shiftable, its position with respect to the guide rod is continually watched to indicate the advance of the cutter into the bone. Upon reaching the desired depth, the rotation is terminated and in this way, a large surfaced perforation of the socket bottom is avoided.

After the socket bed has been prepared, the end milling cutter is removed and, the thread cutter containing also an axially shiftable guide rod is placed in position by inserting the end of the guide rod in the guide bore and rotate it until is has been determined by observing the relative position of the thread cutter with respect to the guide rod that the desired depth has been reached, at which point, the operation is terminated, as a result, there is no danger of a large surfaced perforation of the socket bottom or of any destruction of the thread. Of course, there may be other operations performed in finishing up the socket bed between the use of the milling cutter and thread cutter.

In a further development of the invention, the cutters may be provided with a concentrically located, hollow shaft extending upwardly from the top of the cutter, the interior diameter of the hollow shaft being such as to permit the guide rod to be slidably received therein and the shaft being provided at its upper end with a handle or a coupling for a handle, for the rotation of the tool. Within the space between the upper end of the guide rod and the top of the hollow shaft, a compression spring may be positioned for the purpose of urging the guide rod in a downward direction at all times. In this case, the hollow shaft may be provided with a scale for measuring the relative displacement in an axial direction between the guide rod and the hollow shaft. The guide rod projects downwardly below the bottom of the tool and is provided with a shoulder to limit the extent of its perforation into the bottom of the guide bore with that portion of the guide rod extending below the shoulder being cylindrical in configuration.

In this form of the invention, the guide rod always rests with its shoulder in engagement with the bottom of the intended socket bed. As the body of the cutter penetrates into the hip bone during rotation, the guide rod shifts axially in the hollow space within the shaft and the amount of this shifting can be measured on the scale on the hollow shaft to provide an indication of the amount of penetration of the cutter into the hip bone. Upon reaching the desired depth of penetration regardless of whether one is using the end milling cutter, or using the thread cutter, rotation of the tool is terminated.

Advantageously, the hollow shaft may be provided with at least one longitudinally extending slot within which a cross bolt extending through the guide rod can be received, the axial movement of the bolt in the slot indicating the axial shifting of the relative positions of the two elements whereby a scale can be provided on the outside of the shaft alongside of the slot. Furthermore, it has been found useful to close the upper end of the hollow shaft and to insert a compression spring inside the shaft one end of which bears on the closed end of the shaft, the other end bearing on the top of the guide rod to exert a continuous downward force on the rod.

A further modification of the invention is to leave the upper end of the hollow shaft open and to allow the guide rod to project upwardly above the hollow shaft. In this way, the relative penetration of the cutter with respect to the guide rod is represented by the extent of projection of the guide rod above the upper end of the hollow shaft, and to measure the relative position of the two elements, a scale may be provided on the guide rod since, as the cutter penetrates into the bone, the amount of projection of the rod above the shaft increases.

A further advantage of the invention is the fact that the shoulder provided on the guide rod which limits the insertion of the guide rod into the guide bore hole, can also be used to positively limit the downward movement of the end milling cutter, and for this purpose, an annular recess may be provided in the bottom of the cutter into which said shoulder may be received, as a result of this arrangement, the depth of the cylindrical wall of the socket can be limited precisely to the desired amount.

Other objects and advantages will be evident to those skilled in the art after reading the specification in connection with the annexed drawings in which FIG. 1 is a cross-section of a ceramic socket of the type disclosed and claimed in said copending application Ser. No. 466,640, the present invention being intended, but not exclusively, for making the socket bed used for this type of socket;

FIG. 3 is an elevation, partly in section, of a preferred form of end milling cutter according to the present invention;

FIG. 4 is a view in elevation, partly in section, for forming an annular recess for the shoulder of the socket, and;

Figure 1:
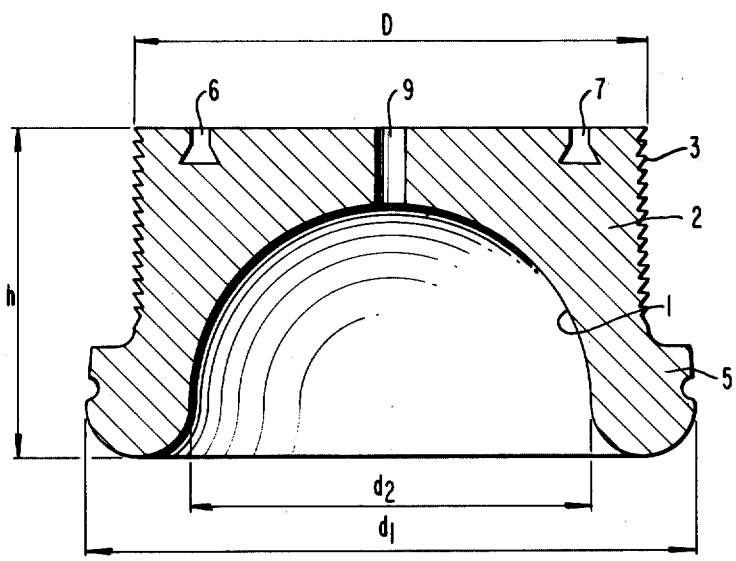
FIG. 1a is a detailed cross-section of the thread on the socket.
Figure 1A:
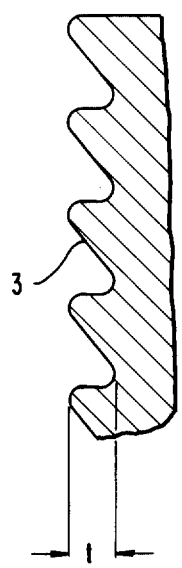
Figure 2:
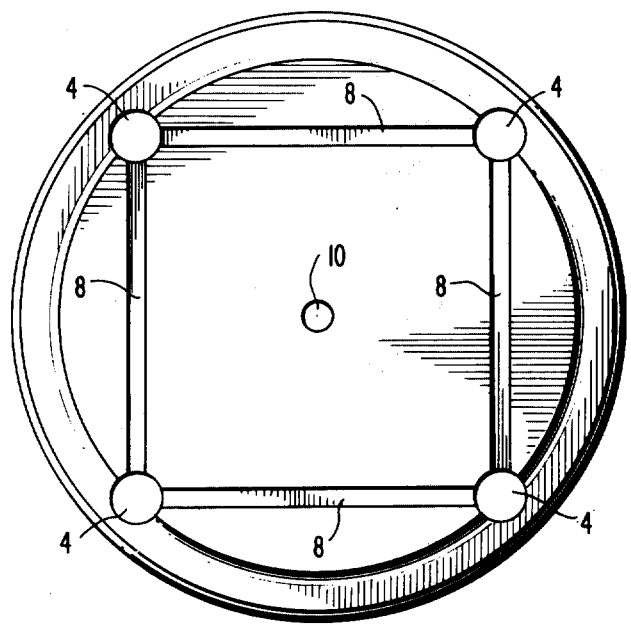
FIG. 2 is a plan view of the socket of FIG. 1.

The threaded socket shown in FIGS. 1 and 2, and which is described and claimed in said copending application Ser. No. 466,640 consists of a body 2 made of a dense aluminum oxide ceramic having an interior approximately hemispherically shaped cavity 1, the surface of which is polished and on which a complementary ball-shaped head of the other member of the hip joint endoprosthesis rests, the ball-shaped head being mounted on a stem which is anchored in the thigh bone. The ball-shaped element is also made of a dense aluminum oxide which is polished to provide a swivelling engagement with the socket with a minimum of friction. The exterior of the body, which engages with the hip bone, is cylindrical having an upper portion whose diameter D is less than the diameter $d1$ of the projecting shoulder 5, but greater than the diameter $d2$ of the hemispherical cavity. The exterior cylindrical part of the socket is provided with a thread 3 and the profile of this thread is formed so that it can transmit forces from the thigh against the inner surface of the socket bed in the hip bone. One example of such a thread is shown in FIG. 1a. In addition, several axially extending grooves 4 are cut in the exterior cylindrical surface, which grooves interupt the thread 3. Four of these grooves are shown in the drawings and they form extensions of circular holes which extend through to the lower side of the shoulder 5. The intersection of the surfaces of the grooves 4 with the threads 3 should be made as sharp-edged as possible to assist in providing a firm engagement between the socket and socket bed when it is inserted. The upper end of the socket is provided with an irregularly profiled surface which consists of a series of dovetailed grooves, indicated by numerals 6 and 7 in FIG. 1 and having flat inner surfaces indicated by numeral 8 in FIG. 2.

In preparing the socket bed to receive the socket shown in FIGS. 1 and 2, it is first necessary to drill a guide bore hole, having a diameter substantially smaller than the diameter of the socket, into the hip bone and at the proper angular inclination, the depth of this bore hole being at least as great as the depth at which the upper surface of the socket will be located. The next step is to use the tool shown in FIG. 3 to make a circular recess in the hip bone having a diameter corresponding to the inner diameter of the exterior thread of the socket. This tool consists of an elongated guide rod 14 having a cylindrical end portion 13 which is inserted into the guide bore hole. This guide rod 14 is shiftably mounted in the end milling cutter 15 whose outer surface is cylindrical and concentric with the axis of the guide rod. Projecting upwardly from the body of the cutter is a hollow shaft 16 which surrounds the guide rod 14, having an upper end 17 extending above the guide rod and is closed at its upper end 18 to provide a space within which a compression spring 19 is seated. This spring bears against the end surface 20 of the upper end 22 of the guide rod with the result that the lower surface 24 of an annular bead 26 at the bottom of the guide rod will always rest on the bottom of the socket bed being prepared.

The upper end of the hollow shaft 16 is provided with a coupling 28, which may be in the form of a hexagon capable of receiving a turning handle (not shown). In operation, the body of the tool 15 being connected with the hollow shaft, if the shaft is turned, the teeth 30 provided on the lower end of the tool will remove material from the bone to form a cylindrical socket bed at the desired angle of implantation which has been predetermined by the previously formed guide bore hole, while the axial position of the guide rod with respect to the bottom of the socket is determined by the position of the lower shoulder surface 24.

The hollow shaft 16 is also provided with two longitudinally extending slots 32 and 34 into which the two ends of a cross bolt 36 project, this bolt being inserted in the guide rod 14. As a result of the advance of the tool body 15 into the hip bone, the cross bolt 36 is shifted in the longitudinal slots 32 and 34 in an upward direction and the amount of this shifting can be determined from a scale 38 provided on the exterior of the hollow shaft. A further indication of the fact that the desired limit of penetration of the tool is furnished by the fact that there is an annular recess 42 provided in the bottom of the body of the tool 15 into which the annular bead 26 of the guide rod will be received when the tool has reached its desired depth. This also positively prevents further advance of the tool and contributes to preventing a large surfaced penetration of the hip bone. After the cylindrical cavity has been prepared, the tool is removed.

For the purpose of forming an annular recess at the open end of the socket bed for the seating of the shoulder 5 of the socket, an edge milling cutter, such as the tool shown in FIG. 4, and having a coupling 28 for a turning handle, can be used.

Figure 5:
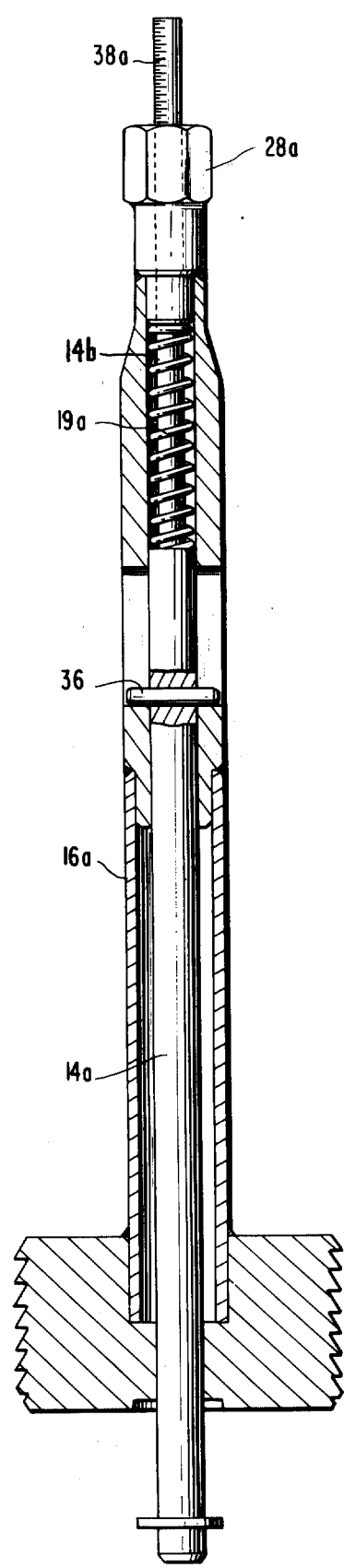
FIG. 5 is an elevation, partly in section, of a preferred form of thread cutter, with a modified form of depth measuring scale, in accordance with the present invention.

The next operation is to cut the desired thread in the cylindrical wall which has previously been prepared by means of thread cutter shown in FIG. 5. This tool is generally similar to the tool of FIG. 3 with the exception that the lower end face of tool body 15 is smooth and the cylindrical exterior surface of the tool body 15 is profiled to cut the type of thread shown in FIG. 1a. However, a modified form of scale for determining the depth of penetration of the thread cutter (FIG. 5) can be used, this modified form being equally adaptable to the end milling cutter of FIG. 3, and vice versa. In the modified form, shown in FIG. 5, the guide rod 14a is longer than the hollow shaft 16a; the upper end 14b of the rod being of reduced diameter for projecting upwardly through the spring 19a and above the upper end of the shaft 16a and coupling 28a; the scale 38a being placed on the projecting upper end of rod 14a. Again, a precaution against excessive penetration is provided by the positive stop action provided by the engagement of the bead 26 in engagement with the recess 40 in the bottom of the tool body.

One or more thread cutting tools, similar to that shown in FIG. 5 may be used, each having progressively deeper cutting surfaces, so as to form a thread of approximately 3mm depth. After that, the bone tissue is carefully washed and the socket of FIGS. 1 and 2 is placed on a reinforced plastic tool having a point which can be fixed in the central hole in the socket (indicated by numeral 9 in FIG. 1 and numeral 10 in FIG. 2) by means of a spreader. The socket may be inserted into the socket bed beyond the soft tissues and "Hohmann levers" into engagement with the thread at the predetermined angle, this instrument is then removed and a four-armed gripping tool is inserted into the openings 4 of the flange 5 of the socket and the socket is anchored in the thread by means of rotation. The final position can be determined because of the flowing of blood from the central hole in the socket and by means of probing through this opening with a small forceps. After the socket has been seated at the bottom of the socket bed, a series of ceramic pegs are hammered into the openings 4 in the socket to prevent any further rotation while the tissues are growing into place in the grooves on the exterior of the socket.

What is claimed is:

1. In a tool for preparing a socket bed in a hip bone for the implantation of the socket of a complete hip joint endoprosthesis, wherein an elongated straight guide bore hole has previously been prepared in said hip bone at the proper inclination for the socket to be inserted which said socket is provided with a threaded exterior surface having a diameter greater than the diameter of said guide bore hole, the improvement which comprises an elongated guide rod to be rotatably received in said guide bore hole, said guide rod being axially, shiftably mounted in a rotary cutter for progressively removing material around said guide bore hole, means for rotating said cutter, and indicia means for measuring the depth of penetration of said cutter with respect to the lower end of the guide rod.

2. The invention defined in claim 1, wherein said cutter includes an upwardly extending, hollow shaft and said guide rod is longer than the hollow shaft, said rod projecting above the upper end of said shaft, said indicia means comprising scale means on the upper end of said rod.

3. The invention defined in claim 1, wherein said cutter includes an upwardly extending, hollow shaft provided with means for rotating the shaft and tool, said shaft surrounding at least a portion of said guide rod, spring biassing means for urging the rod in a downward direction, said rod including a shoulder adjacent the lower end to limit penetration of the rod into the lower end of the guide bore hole, at least that portion of the rod below the shoulder being cylindrical, said indicia means comprising scale means on said shaft.

4. The invention defined in claim 3, wherein said shoulder comprises an annular bead surrounding the rod and the lower end of said cutter is provided with an annular recess into which said bead can be received.

5. The invention defined in claim 3, wherein said hollow shaft is provided with at least one longitudinal slot, said rod being provided with a radial projection slidable in said slot, said indicia means including a scale extending axially of the hollow shaft adjacent to said slot.

6. The invention defined in claim 5, wherein said spring biassing means comprises a compression spring contained within the upper end of said hollow shaft, one end of the spring bearing on the upper end of said rod.

7. Method for the cement-free implantation of a threaded artificial socket for a complete endoprosthesis comprising the steps of:
   a. preparing an elongated, small diameter guide bore hole in the hip bone at the proper inclination for the implanted socket and extending to a depth at least equal to the bottom surface level at which the socket will be implanted;
   b. inserting an elongated guide rod into said guide bore hole;
   c. placing an end milling cutter on said guide rod in slidable relationship to said rod and enlarging the opening in said hip bone by rotating said cutter concentrically about the axis of the guide rod, and;
   d. controlling the depth of penetration of said cutter by comparing the relative axial position of the cutter with respect to the guide rod.

8. Method of claim 7 which includes the additional step of:
   e. removing said end milling cutter from said guide rod;
   f. replacing said end milling cutter with a rotatable thread cutter, and;
   g. rotating said thread cutter about the axis of said guide rod and determining the depth of penetration of said thread cutter by a comparison of the relative displacement of the cutter with respect to the guide rod.

9. Method of claim 8 which includes the additional step of:
   h. removing said thread cutter from the guide rod;
   i. screwing in said threaded socket to the proper depth, and;
   j. inserting an element in the hip bone to prevent further rotation of said socket while implanted.

10. Method of claim 9, wherein the element inserted in step (j) consists of at least one peg which is inserted in an axial direction into the hip bone through an opening provided in the socket.

* * * * *